United States Patent [19]
Hart

[11] Patent Number: 5,827,304
[45] Date of Patent: Oct. 27, 1998

[54] INTRALUMINAL EXTRACTION CATHETER

[75] Inventor: Charles C. Hart, Huntington Beach, Calif.

[73] Assignee: Applied Medical Resources Corporation, Laguna Hills, Calif.

[21] Appl. No.: 559,076

[22] Filed: Nov. 16, 1995

[51] Int. Cl.⁶ .............................. A61B 17/22; A61D 1/02
[52] U.S. Cl. ..................... 606/159; 606/128; 606/170; 606/194; 604/104; 604/107; 604/267; 604/35; 600/571
[58] Field of Search .................................. 604/22, 27, 35, 604/48, 96, 101, 104, 105–109, 266, 267, 264, 280; 606/191, 192, 194, 198, 200, 159, 167, 170, 127, 128; 128/767–769, 759, 758, 757; 600/580–582, 570–572

[56] References Cited

U.S. PATENT DOCUMENTS

| | | | |
|---|---|---|---|
| 3,435,826 | 4/1969 | Fogarty. | |
| 3,896,815 | 7/1975 | Fettel et al.. | |
| 3,978,863 | 9/1976 | Fettel et al.. | |
| 3,996,938 | 12/1976 | Clark III | 606/200 |
| 4,089,506 | 5/1978 | Blake. | |
| 4,650,466 | 3/1987 | Luther | 604/105 |
| 4,885,003 | 12/1989 | Hillstead | 604/107 |
| 4,921,484 | 5/1990 | Hillstead | 606/159 |
| 4,950,238 | 8/1990 | Sullivan. | |
| 4,979,939 | 12/1990 | Shiber | 606/159 |
| 5,074,871 | 12/1991 | Groshong | 604/107 |
| 5,152,771 | 10/1992 | Sabbaghian et al. | 606/198 |
| 5,246,445 | 9/1993 | Yachia et al. | 604/104 |
| 5,279,565 | 1/1994 | Klein et al. | 606/198 |
| 5,411,509 | 5/1995 | Hilal | 606/159 |

FOREIGN PATENT DOCUMENTS

| | | | |
|---|---|---|---|
| 0448859 | 10/1991 | European Pat. Off. | 606/159 |
| 9102494 | 3/1991 | WIPO | 606/159 |

*Primary Examiner*—Ronald Stright
*Attorney, Agent, or Firm*—Richard L. Myers

[57] ABSTRACT

The expandable intraluminal catheter is used for removing occlusive material from a body passage. The catheter includes a handle having both a proximal handle end and a distal handle end. Attached to the distal handle end is an elongate tubular body, which includes a proximal elongate tubular body end and a distal elongate tubular body end. The elongate tubular body further includes a lumen between the proximal elongate tubular body end and the distal elongate tubular body end. A number of radially-expandable segments are disposed on the elongate tubular body near the distal elongate tubular body end. These radially-expandable segments can be mechanically activated by a user when the distal elongate tubular body end is within a blood vessel, to thereby contact and partition occlusive material within the blood vessel. The partitioned occlusive material within the blood vessel can then be removed.

18 Claims, 9 Drawing Sheets

INTRALUMINAL EXTRACTION CATHETER

BACKGROUND OF THE INVENTION

The present invention relates generally to catheters and, more particularly, to an expandable intraluminal catheter for removing occlusive material from a body passage.

Expanding diameter catheters are commonly used in surgical procedures. A well-known mechanism for expanding the diameter of the catheter is inflation. These balloon-type embolectomy catheters are disclosed in U.S. Pat. No. 3,435,826, U.S. Pat. No. 3,467,101, and U.S. Pat. No. 5,320,604 for use in removing blood clots and thrombus from blood vessels. In addition to balloon-type embolectomy catheters, other mechanisms have been proposed by the prior art in an attempt to improve the procedure of removing clots and thrombus or plaque from blood vessels. U.S. Pat. No. 5,282,484 and U.S. Pat. No. 5,284,486 disclose a catheter having rotating blades. U.S. Pat. No. 5,370,653 discloses a catheter having a brush for removal of material from a blood vessel. U.S. Pat. No. 5,192,290, which is assigned to the assignee of the present invention, discloses a catheter having an expanding elastomeric foam.

All of these prior art embolectomy catheters have intrinsic problems and complications connected with use in delicate blood vessels, regardless of whether balloons, blades, or bushes are used. Balloons may rupture or may transmit excessive force to the delicate blood vessel. Blades or brushes may cause extensive damage to the fragile lining of the delicate blood vessel. An elastomeric foam member, such as that disclosed in U.S. Pat. No. 5,192,290, provides a mechanical activation of the expansion means. Although this mechanical activation provides a safety measure by giving the user a tactile feel, the elastomeric foam expansion member does not have the removal capabilities of the above-mentioned balloons, blades, and brushes.

Another problem commonly shared by all of the prior art embolectomy catheters stems from a removal method which is inherently engineered into these devices. A common principle is implemented by each of the prior art devices. Specifically, the expanding members of these prior art devices are advanced beyond the occlusive material to be removed or treated in the blood vessel, and the occlusive material is then forced as a whole along a retrieval path through the blood vessel to a collection site. If the occlusive material is well-attached to the blood vessel wall, the shear forces required to dislodge this material may be damaging to the blood vessel. Since the expanding member basically contacts a perimeter portion of the occlusive material and pushes this material through the vessel to the collection site, a resulting compression of the occlusive material often results. This compression may necessitate the application of additional, excessive force for the removal of the occlusive material, resulting in further damage to the delicate intimal lining of the blood vessel. A need thus exists in the prior art for an embolectomy catheter, that is able to capture and remove occlusive material from a delicate blood vessel without damaging the intimal lining or causing traumatic injury to that blood vessel.

SUMMARY OF THE INVENTION

The expansion member of the intraluminal catheter of the present invention harnesses a mechanical activation of the expansion member, and thus does not suffer from the problems associated with prior art balloons, blades, and brushes. This mechanical activation of the expansion member provides the user with a tactile feel. Additionally, the expandable intraluminal catheter of the present invention does not rely on the removal mechanism of the prior art. Specifically, the expandable intraluminal catheter of the present invention does not contact and push only the outer parameter of the occlusive material in the blood vessel. The expandable intraluminal catheter of this invention contacts the occlusive material along the entire length of the occlusive material within the blood vessel to thereby minimize the compression effect suffered by the prior art. The resulting force required to dislodge or mobilize the occlusive material at any one point within the blood vessel is significantly reduced, since compression is reduced and the mobilizing force is distributed over a large surface area. Since the occlusive material is contacted, and partitioned, at a number of points along the length of the occlusive material within the blood vessel, a risk that the occlusive material may be lost, left behind, or swept into the flow of the blood vessel is also reduced.

The expandable intraluminal catheter is used for removing occlusive material from a body passage. The catheter includes a handle having both a proximal handle end and a distal handle end. Attached to the distal handle end is an elongate tubular body, which includes a proximal elongate tubular body end and a distal elongate tubular body end. The elongate tubular body further includes a lumen between the proximal elongate tubular body end and the distal elongate tubular body end. A number of radially-expandable segments are disposed on the elongate tubular body near the distal elongate tubular body end. These radially-expandable segments can be mechanically activated by a user when the distal elongate tubular body end is within a blood vessel, to thereby contact and partition occlusive material within the blood vessel. The partitioned occlusive material within the blood vessel can then be removed. The mechanism for mechanically activating the radially-expandable segments includes a wire disposed within the lumen of the elongate tubular body. A proximal end of the wire is connected to the proximal handle end, and a distal end of the wire is connected to the distal elongate tubular body end. This connection of the wire between the handle and the distal elongate tubular body end fixes the length therebetween. An actuator, connected to the proximal elongate tubular body end, can be actuated by the user to move the proximal elongate tubular body end toward the relatively stationary distal elongate tubular body end. This movement results in an expansion of the radially-expandable segments. Similarly, the user can reverse the direction of the actuator to increase the distance between the proximal elongate tubular body end and the distal elongate tubular body end to thereby decrease the diameters of the radially-expandable segments.

In addition to the partitioning effect caused by the number of radially-expandable segments contacting the occlusive material at a corresponding number of points within the blood vessel, the expandable intraluminal catheter of the present invention utilizes a peristaltic effect among the number of radially-expandable segments. Specifically, the radially-expandable segments closer to the distal elongate tubular body end may be configured to expand before other radially-expandable segments adjacently proximal thereto. This progressive deployment of the radially-expandable segments captures and mobilizes the occlusive material, progressively, in a direction toward the collection site.

These radially-expandable segments may be formed of a tubular woven, braided, or meshed material having tiny apertures therein. When the radially-expandable segments are activated, the small apertures become larger to thereby allow for liquids or small particles to pass therethrough. Thus, solvents or other medications may be administered through the lumen of the expandable intraluminal catheter, to thereby exit through the apertures of the radially expandable members. Suction may also be applied through the lumen to draw fluids back through the apertures. This suction may aspirate, desiccate, or in other ways mechanically attach portions of chemically treated occlusive material to the radially-expandable segments to thereby facilitate removal of the occlusive material from the blood vessel.

The mechanical activation of the plurality of radially-expandable segments, in addition to providing a tactile feel to the user, provides an expansion mechanism which has a relatively smooth outer surface for non-destructive insertion into the blood vessel, and subsequently provides relatively rigid enlarged-diameter segments for removal of the occlusive material from the blood vessel. According to another feature of the present invention, an expandable distal member, formed of elastomeric foam, can be placed at the distal elongate tubular body end of the expandable intraluminal catheter tube to further facilitate effective removal of the occlusive material from the blood vessel.

The present invention, together with additional features and advantages thereof, may best be understood by reference to the following description taken in connection with the accompanying illustrative drawings.

BRIEF DESCRIPTION OF THE DRAWINGS

FIG. 5a is an enlarged view of the handle portion of the expandable intraluminal catheter in the position shown in FIG. 3a;

DETAILED DESCRIPTION OF THE PREFERRED EMBODIMENTS

Figure 1A:
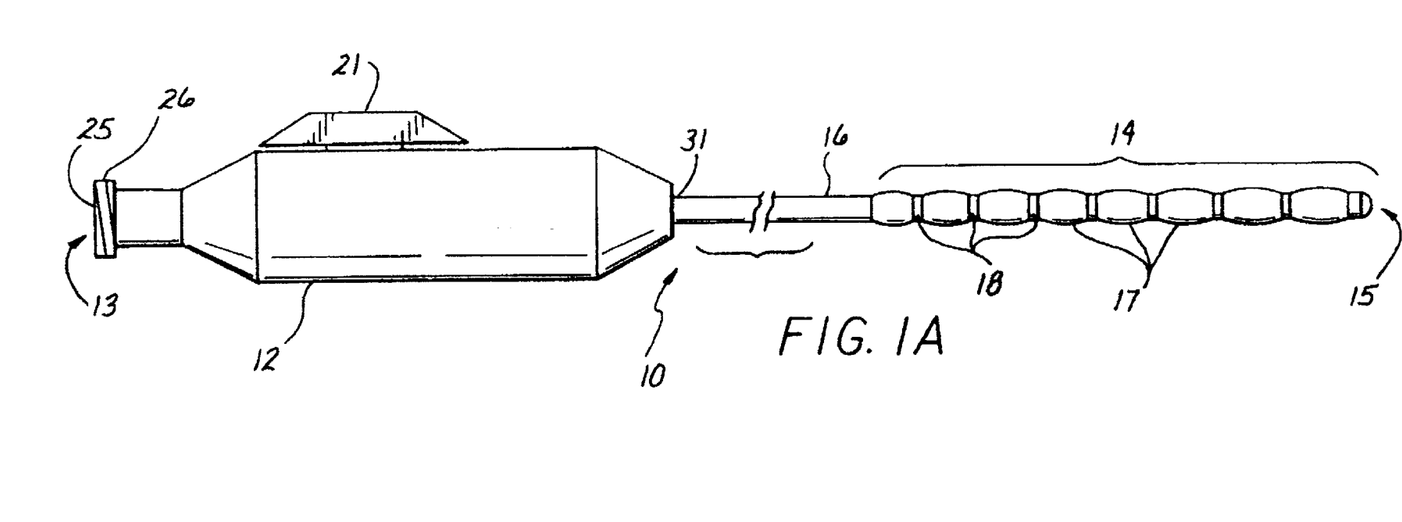
FIG. 1a is a side view of the expandable intraluminal catheter of the presently preferred embodiment in an undeployed configuration.
Figure 1B:
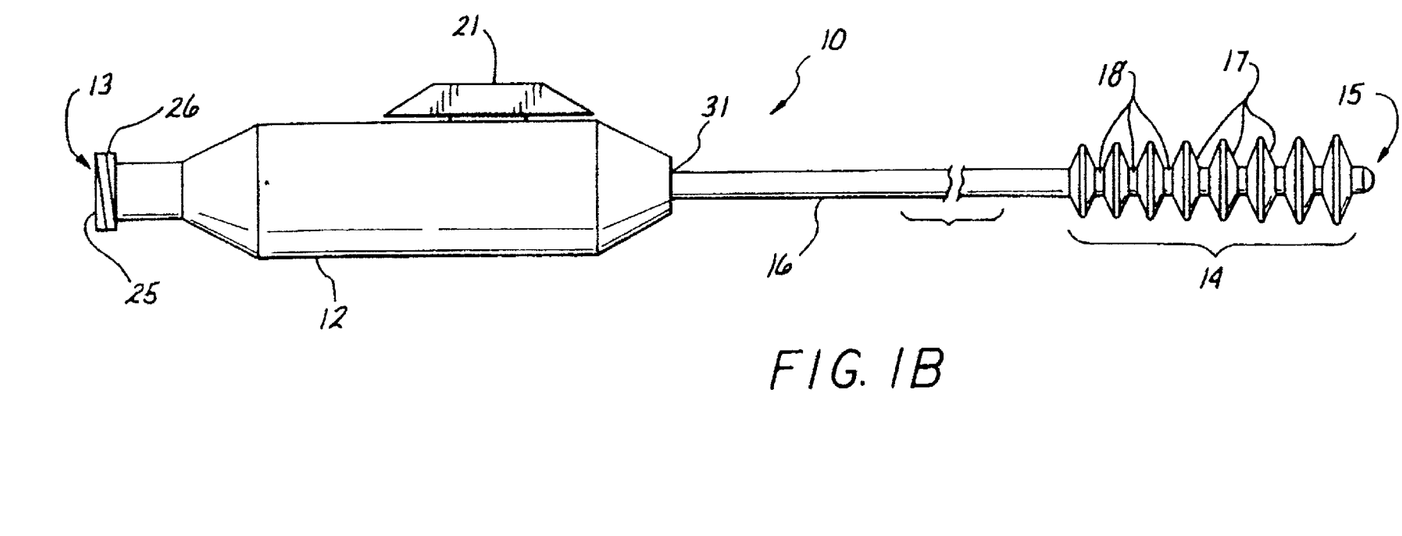
FIG. 1b is a side view of the expandable intraluminal catheter of the presently preferred embodiment in a deployed or expanded configuration.

An expandable intraluminal catheter of the presently preferred embodiment is illustrated in FIG. 1 and designated generally by the reference numeral 10. The expandable intraluminal catheter 10 comprises a handle 12 and an elongate tubular body 16. The elongate tubular body 16 fits into an aperture 31 of the handle 12. A segmented distal portion 14 is located near the distal end 15 of the elongate tubular body. This segmented distal portion 14 preferably comprises a number of expandable segments 17 separated by a number of non-expandable segments 18. Each expandable segment 17 preferably comprises a tubular woven, braided, or meshed material. Each of the non-expandable segments preferably comprises a semi-rigid plastic tubing. The handle 12 is configured to be gripped by the hand of a user, and the actuator 21 is movable between a reverse position shown in FIG. 1a and a forward position shown in FIG. 1b. An opening or port 25 is located at the proximal end of the handle 12. This opening 25 preferably comprises a leur-type locking hub 26.

As shown in FIG. 1b, movement of the actuator 21 into the forward position results in an expansion of the expandable segments 17. As each expandable segment 17 radially expands, a corresponding width of that expandable segment, measured in the direction of a longitudinal axis of the elongate tubular body 16, decreases. The non-expandable segments 18 do not radially expand upon movement of the actuator 21 into the forward position and, further, do not decrease in width, measured along the longitudinal axis of the elongate tubular body 16.

Figure 2A:
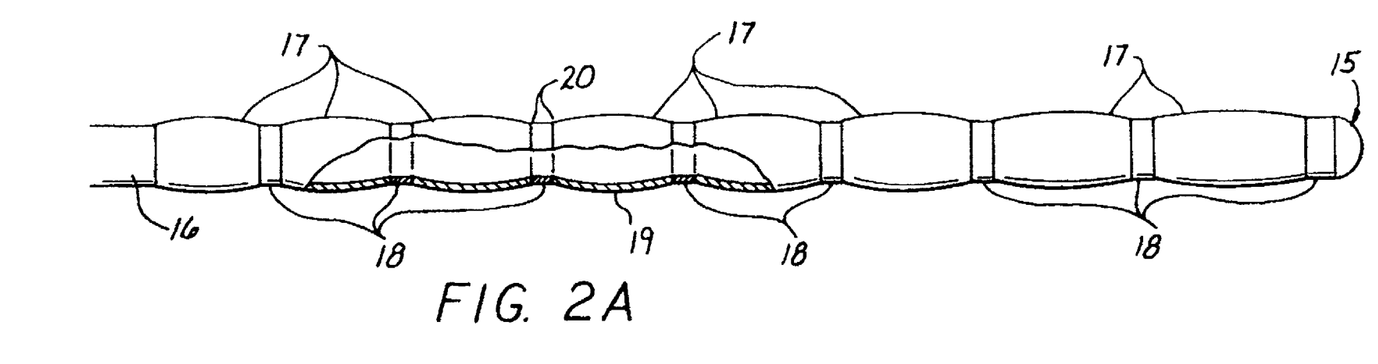
FIG. 2a is a partial cross-sectional view of the expandable intraluminal catheter of the presently preferred embodiment in the undeployed configuration.

FIG. 2a illustrates a closer view of the segmented distal portion 14 of the elongate tubular body 16 in the non-activated configuration. In the presently preferred embodiment, the expandable segments 17 and the non-expandable segments 18 are formed of different materials, but comprise a generally continuous wall 19. The expandable segments 17 and the non-expandable segments 18 are fused together at fusion points 20 along the longitudinal axis of the tubular elongate body 16. Alternatively, a single expandable material may be fused at the fusion points 51, or non-expandable bands may be placed around the wall 19 to form the non-expandable segments 18. In the presently preferred embodiment, the locations of the fusion points 20 along the longitudinal axis of the elongate tubular body 16 are selected to correspond to predetermined expansion ratios. Each of the fusion points 20 is thus positioned to yield a deployed cone-shaped expandable segment 17 (FIG. 2b) of a predetermined diameter and circumference.

Figure 2B:
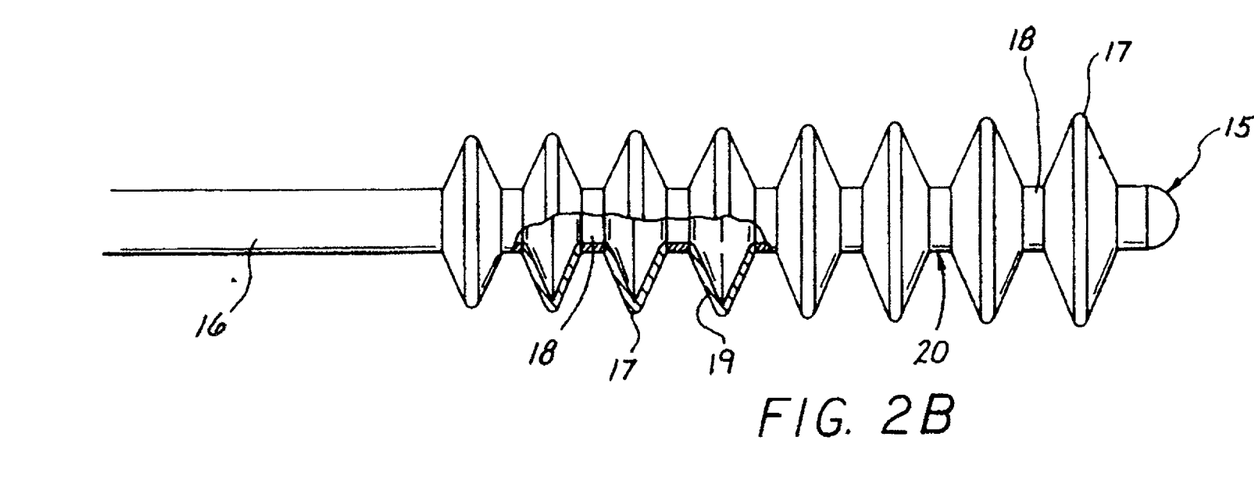
FIG. 2b is a partial cross-sectional view of the distal portion of the expandable intraluminal catheter in an expanded configuration, according to the presently preferred embodiment.

In the presently preferred embodiment, the width of the expandable segments 17, measured along the longitudinal axis of the elongate tubular body 16, are progressively larger in the direction toward the distal end 15. This larger width of the expandable segments 17 in the direction of the distal end 15 results in expandable segments 17 near the handle 12 having smaller widths than expandable segments 17 near the distal end 15. As shown in FIG. 2b, the expandable segments 17 near the distal end 15 with larger widths expand to greater diameters when activated, than the expandable segments 17 near the handle 12.

Figure 2C:
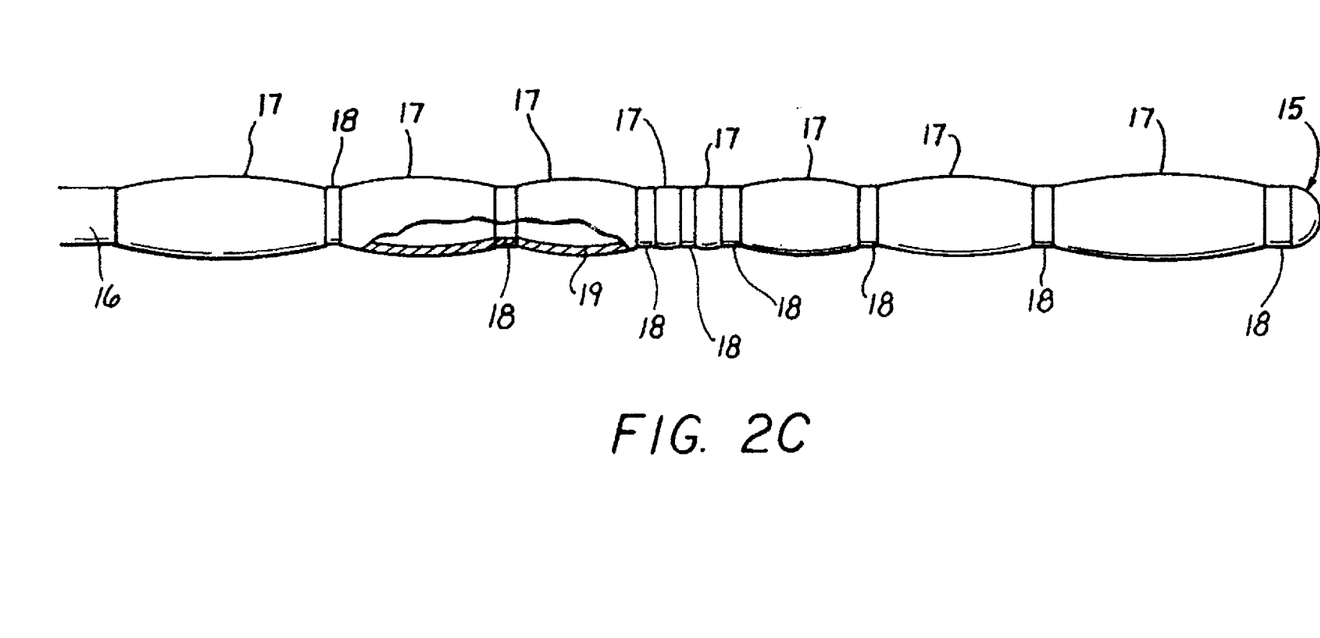
FIG. 2c is a partial cross-sectional view of the distal portion of an expandable intraluminal catheter in the undeployed configuration and shown having segments of differing widths.
Figure 4:
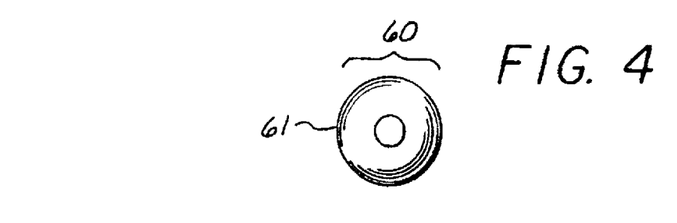
FIG. 4 is a distal-end view of the expandable intraluminal catheter in the expanded configuration, according to the presently preferred embodiment.

FIG. 4 illustrates the segmented distal portion 14 in an expanded configuration, as shown on the distal end 15 looking down toward the handle 12. Each expandable segment 17 has a progressively smaller diameter 60 and circumference 61, according to its location away from the distal end 15. According to the presently preferred embodiment, the braided material which comprises the wall 19 has a characteristic which causes the expandable segments 17 having larger widths to expand before the expandable segments 17 having smaller widths. According to this presently preferred embodiment, a progressive deployment or expansion of the expandable segments 17 occurs upon activation by the actuator 21, in the direction from the distal end 15 toward the handle 12, to thereby capture and mobilize occlusive material 52 (FIG. 6a) in a rearward direction toward the handle 12. The progressive deployment may also be from the distal and handle ends 15 and 12 to the center of the expandable segments 17 (FIG. 2c).

Figure 3A:
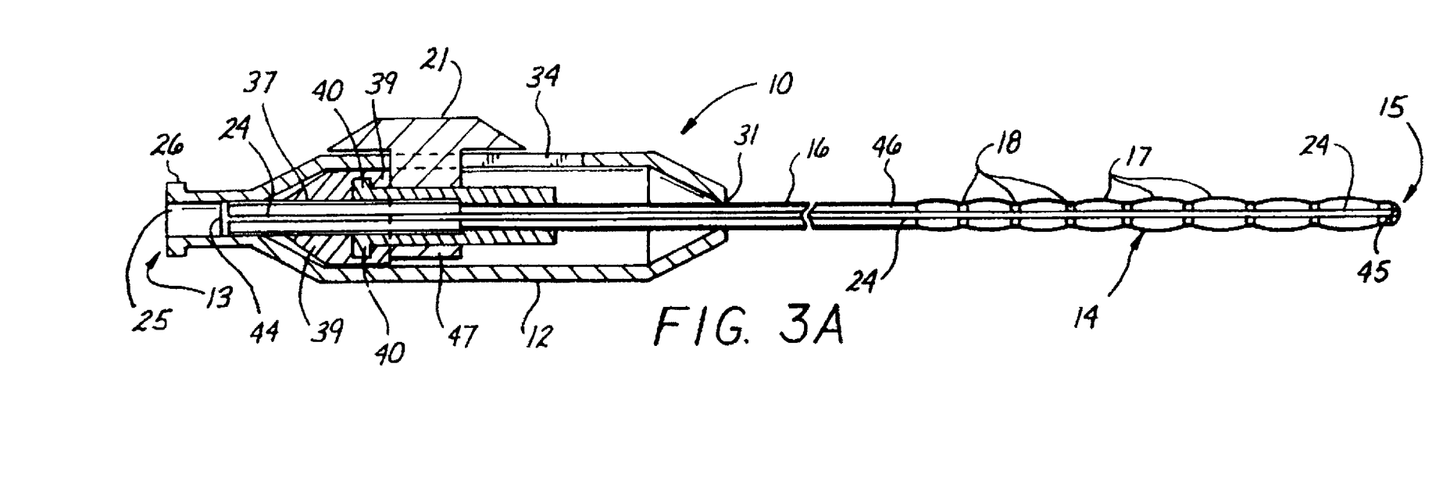
FIG. 3a is a cross-sectional view of the expandable intraluminal catheter in an undeployed condition, according to the presently preferred embodiment.
Figure 3B:
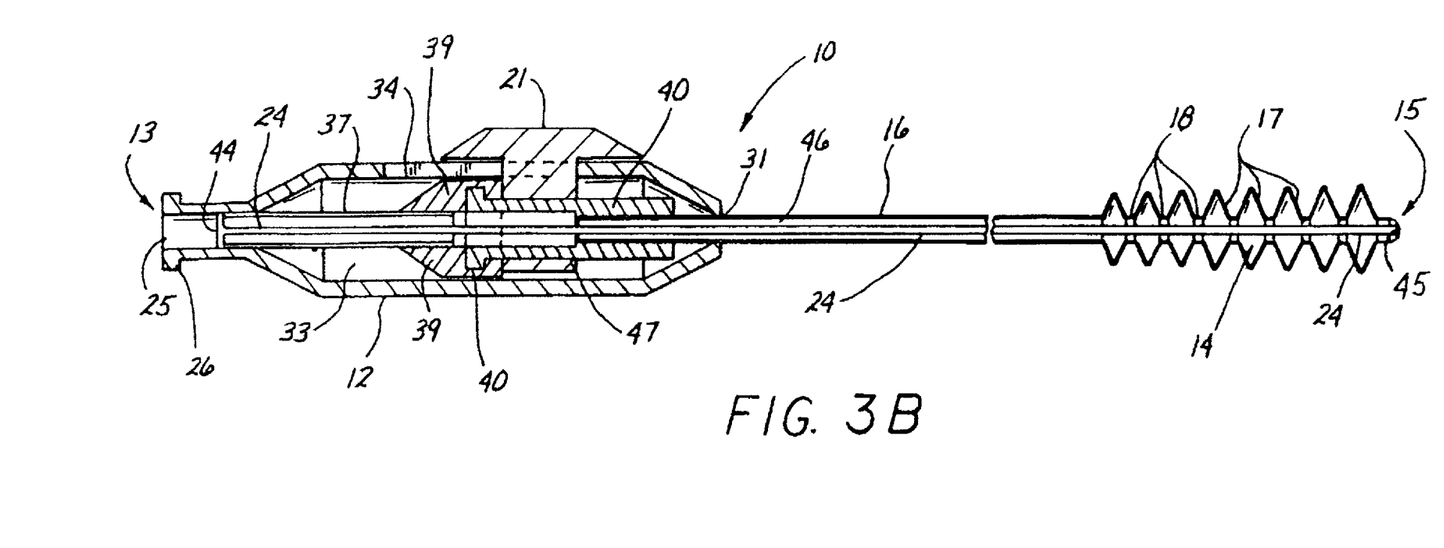
FIG. 3b is a cross-sectional view of the expandable intraluminal catheter in a deployed condition, according to the presently preferred embodiment.

Turning to FIGS. 3a and 3b, a cross-sectional view of the expandable intraluminal catheter 10 is illustrated in both a non-expanded and an expanded configuration, respectively. The elongate tubular body 16 fits through the aperture 31 in the handle 12 and extends through the handle 12 to the proximal end 13. A wire 24 fits within a lumen 46 of the elongate tubular body 16. The wire 24 is connected to a distal connection point 45 at the distal end 15 of the elongate tubular body 16, and is also connected at a proximal point 44 within the handle 12. The wire 24 maintains a relatively fixed distance between the handle 12 and the distal connection point 45. The actuator 21 slides within the slot 34 between the backward position (FIG. 3a) and the forward position (FIG. 3b). This actuator 21 comprises a portion 47 which extends into the handle 12. The portion 47 of the actuator 21 connects to a cylindrical bushing 40. The cylindrical bushing 40 is connected to the elongate tubular body 16, to thereby cause movement of the elongate tubular body 16 along the longitudinal axis of the elongate tubular body 16 with corresponding forward and reverse movement of the actuator 21 within the slot 34.

The cylindrical bushing 40 is connected at its proximal end to an elastomeric gasket or seal 39. A fixed tubular structure 37 is secured to the proximal point 44 at the handle 12. The cylindrical bushing 40 and the elastomeric gasket 39 slidably fit around the fixed tubular structure 37. Thus, movement of the actuator 21 from the reverse position (FIG. 3a) to the forward position (FIG. 3b) causes the bushing 40 and elastomeric gasket 39 to move along an outer surface of the fixed tubular structure 37 in the direction of movement of the actuator 21. The elastomeric gasket 39 maintains a seal between the lumen 46, which extends into the fixed tubular structure 37, and the general interior 33 of the handle 12. A watertight seal is thus formed from the opening 25, through the fixed tubular structure 37, elastomeric gasket 39, cylindrical bushing 40, and the elongate tubular body 16.

Figure 5A:
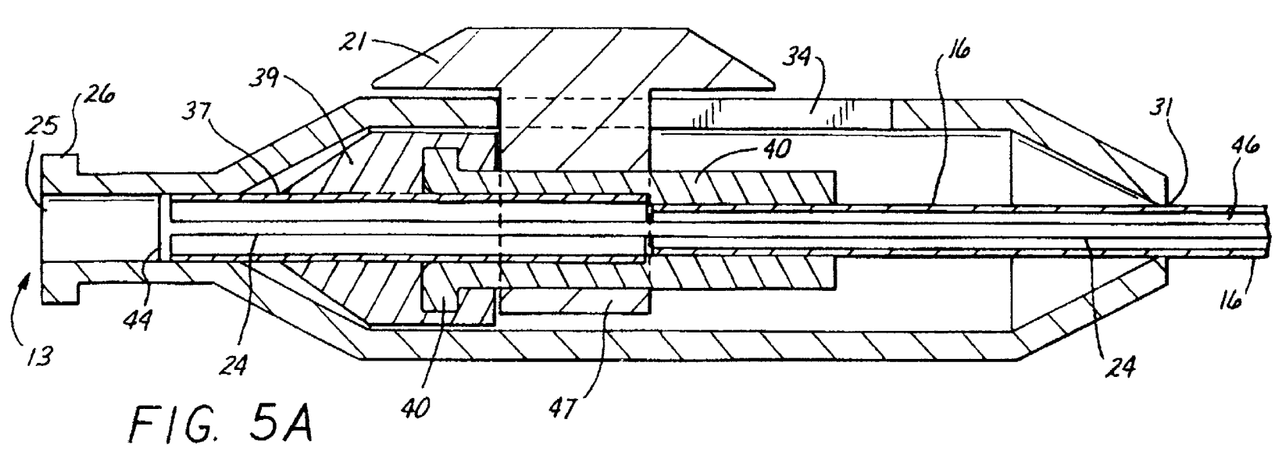
Figure 5B:
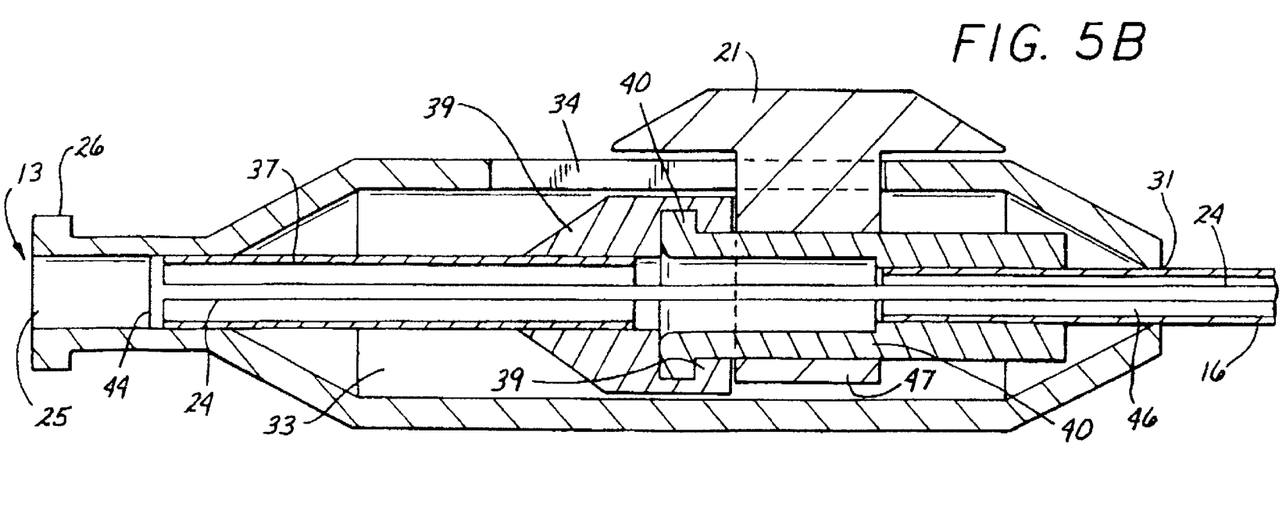
FIG. 5b is an enlarged view of the handle portion of the expandable intraluminal catheter in the position shown in FIG. 3b.

Movement of the actuator 21 toward the distal end 15 moves the end of the elongate tubular body 16, which is attached to the cylindrical bushing 40, toward the distal end 15. Thus, movement of the actuator 21 toward the distal end 15 results in a corresponding movement of the proximal elongate tubular body end toward the distal elongate tubular body end 15. The distal elongate tubular body end 15 does not move forward with forward movement of the actuator 21, since the wire 24 maintains the distance between the distal elongate tubular body end 15 and the handle 12. The reduction in distance between the proximal elongate tubular body end and the distal elongate tubular body end 15 results in a compression of the segmented distal portion 14 from the relatively smooth, small-diameter configuration (FIG. 3a) to the larger diameter configuration (FIG. 3b). In other words, forward movement of the actuator 21 applies a compressive force to the segmented distal portion 14, which is relieved by expansion of the expandable segments 17, as the width of the expandable segments 17 decrease along the longitudinal axis of the elongate tubular body 16. FIGS. 5a and 5b are enlarged cross-sectional views of the handle 12 of FIGS. 3a and 3b, respectively.

Figure 6A:
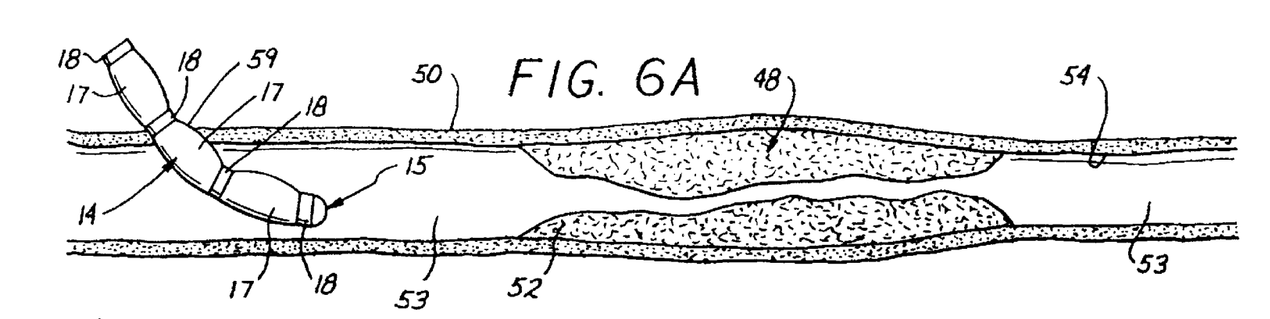
FIGS. 6a–6c illustrate the use of the expandable intraluminal catheter of the present invention to remove occlusive material from a body passage.
Figure 6B:
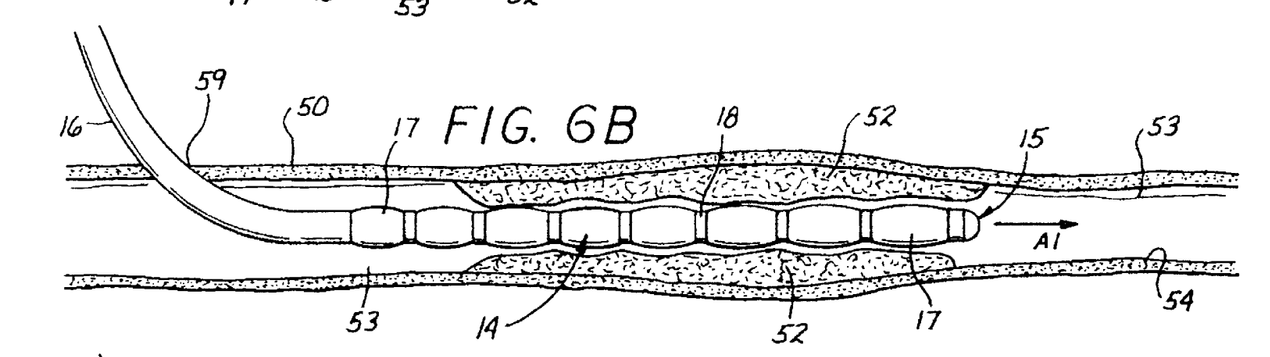
Figure 6C:
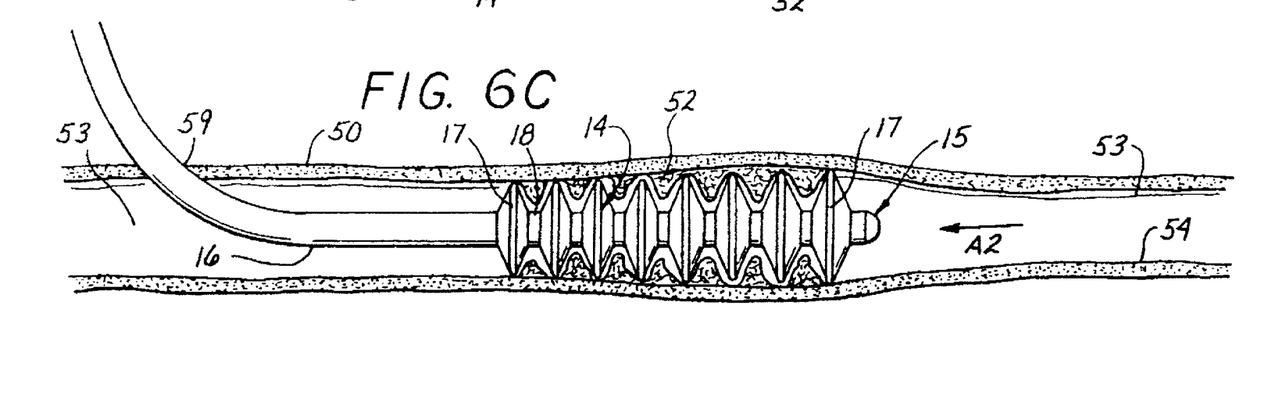
Figure 7A:
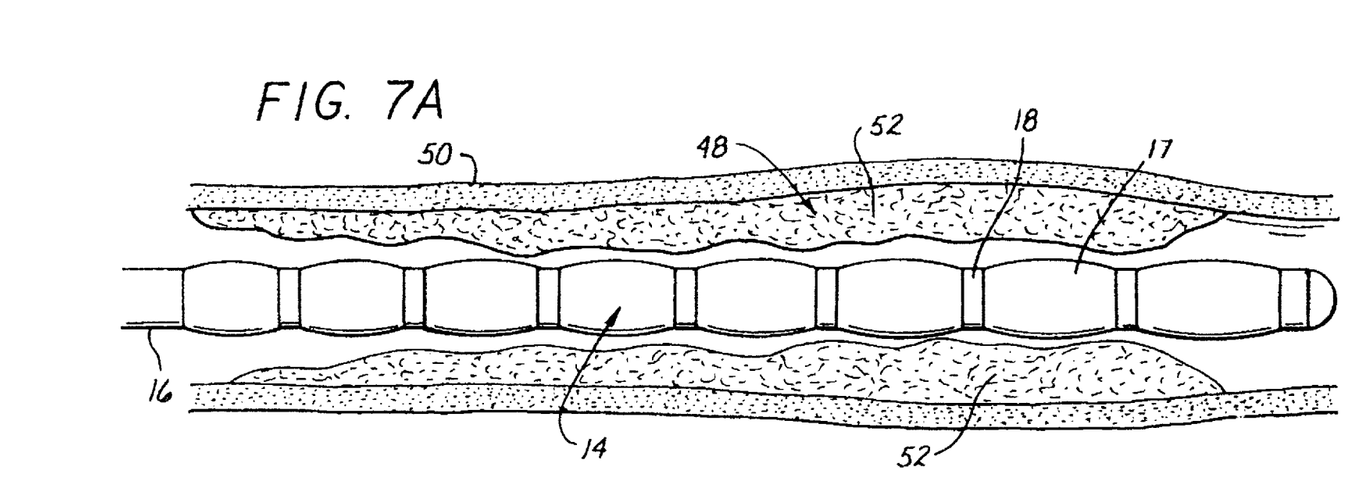
FIG. 7a and 7b are enlarged views of FIGS. 6b and 6c, respectively.
Figure 7B:
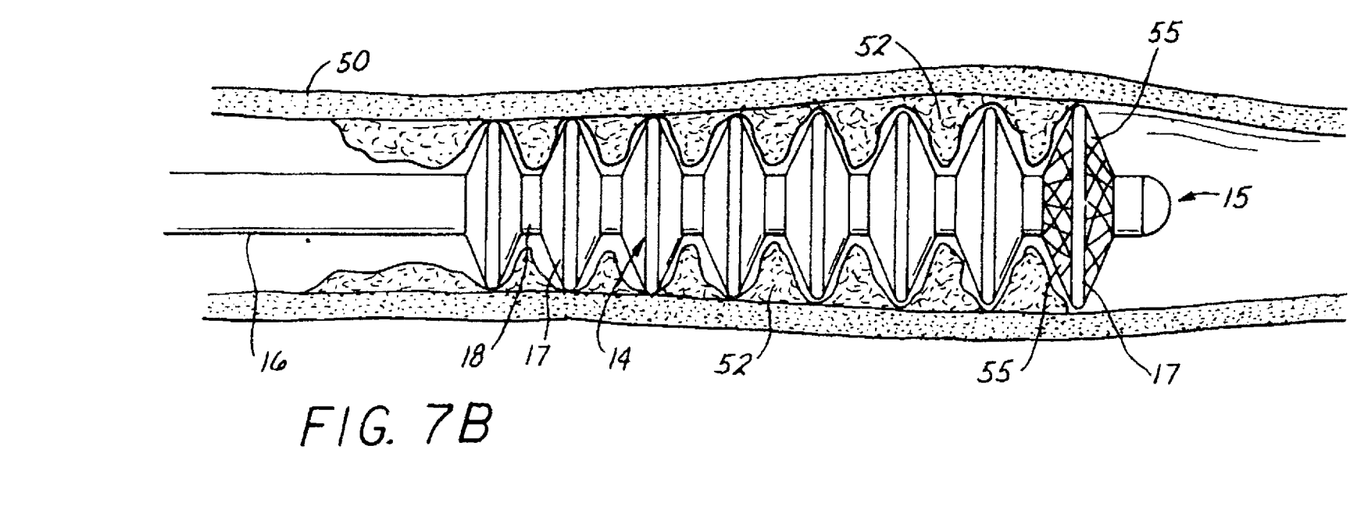
Figure 8A:
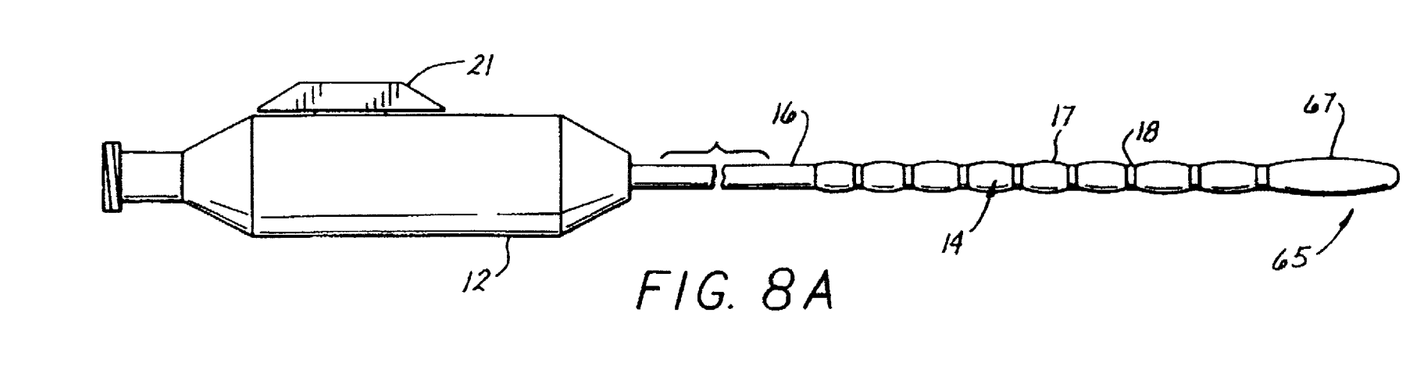
FIGS. 8a and 8b are side views of the expandable intraluminal catheter with an elastomeric expandable foam member attached thereto, according to an alternative embodiment of the present invention.
Figure 8B:
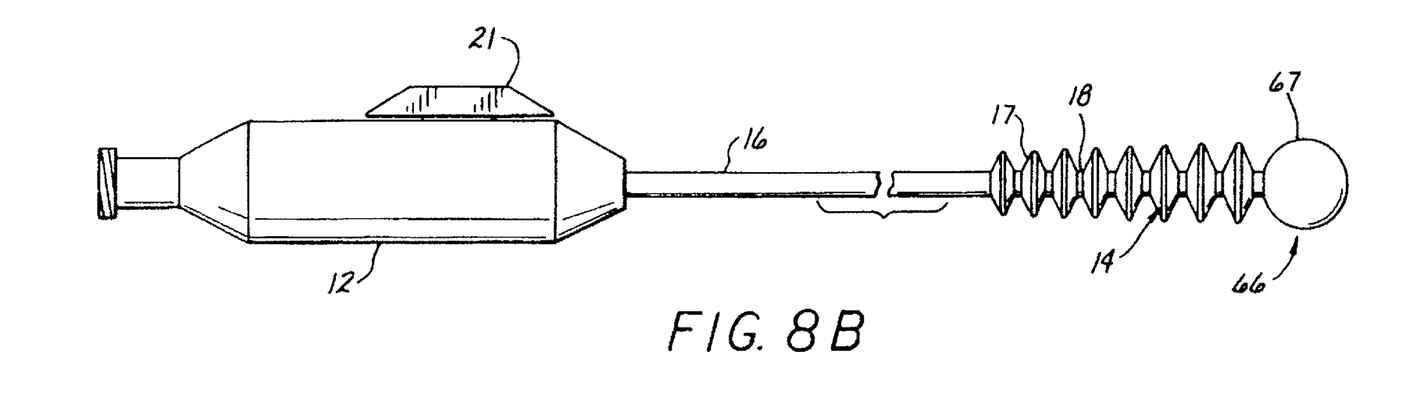

Turning to FIG. 6a, the segmented distal portion 14 of the elongate tubular body 16 is inserted through an incision or puncture 59 of a body passage 50. The body passage 50 may comprise a blood vessel, for example, having occlusive material 52 within the lumen 53 at an operation site 48. The occlusive material may be plaque, thrombi, emboli, or other potential clotting agents within the body passage 50. The segmented distal portion 14 is guided by the interior wall 54 of the body passage 50 to the operation site 48. As shown in FIG. 6b, the segmented distal portion 14 is inserted through the occlusive material 52 with relative ease, since the expandable segments 17 and the non-expandable segments 18 have relatively similar diameters and circumferences. The expandable segments 17 are mechanically activated by the actuator 21 to thereby radially expand, as shown in FIG. 6c. These expandable segments 17 sequentially expand in the direction from the operation site 48 toward the incision 59, to sequentially fill the lumen 53 and partition the occlusive material 52. Thus, once the distal end 15 is moved in the direction of arrow A1 beyond the occlusive material 52, the expandable segments 17 are radially expanded by the compression force resulting from forward movement of the actuator 21. The expandable segments 17 mobilize and capture the occlusive material 52 on a plurality of points along the interior wall 54. The method of mobilization and capture of the occlusive material 52 may be accomplished in several ways. The expandable segments 17 may be radially expanded and radially contracted to mechanically loosen the occlusive material 52 from the interior walls 54 of the body passage 50. Additionally, solvents or other medications may be administered through apertures formed in the expandable segments 17. These fluids are inserted through the opening 25 (FIG. 1) of the expandable intraluminal catheter 10 and guided through the lumen 46 toward the segmented distal portion 14. FIGS. 7a and 7b illustrate closer views of FIGS. 6b and 6c. As shown in FIG. 7b, the apertures 55 in the expandable segments 17 closest to the distal end 15, for example, allow the fluids to exit from the lumen 46 into the interior of the body passage 50. A suction may be applied to the opening 25 to remove the chemically treated occlusive material 52. The occlusive material 52 may thus be aspirated, desiccated, or in other ways mechanically attached to the expandable segments 17 by the negative internal pressure within the lumen 46.

Figure 9A:
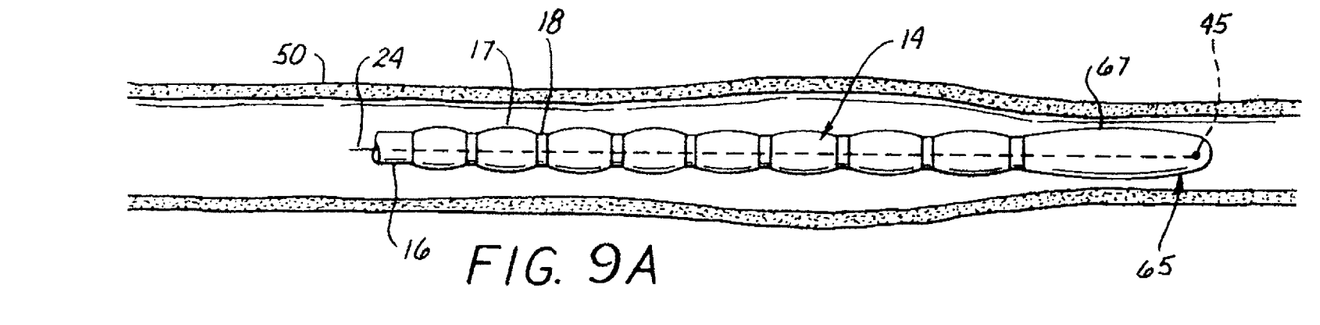
FIGS. 9a and 9b illustrate use of the expandable intraluminal catheter within a blood vessel, according to the alternative embodiment.
Figure 9B:
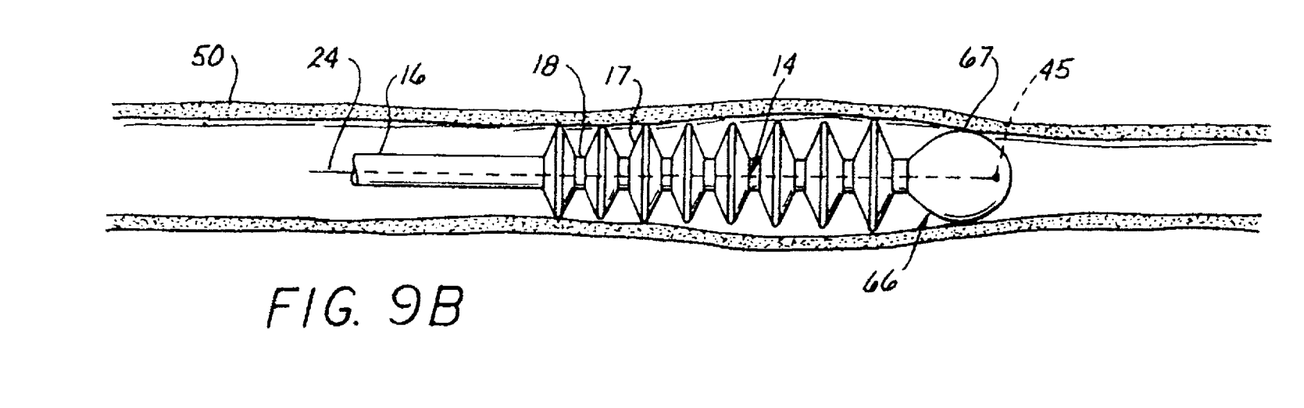

FIG. 9 illustrates the expandable intraluminal catheter 10 according to an alternative embodiment. This configuration comprises an expandable-contractible distal member 67 of an elongated shape 65. When the actuator 21 is moved to the forward position, the distal member 67 is compressed into a generally spherical shape 66. This expandable-contractible distal member 67 preferably comprises an elastomeric foam. The action required to perform the stretching and compression of this expandable-contractible distal member 67 is the same action required to expand and contract the expandable segments 17. The expandable-contractible distal member 67 provides an additional function of further cleaning and removing small pieces of the occlusive material 52.

Although exemplary embodiments of the invention have been shown and described, many other changes, modifications and substitutions, in addition to those set forth in the above paragraph, may be made by one having ordinary skill in the art without necessarily departing from the spirit and scope of this invention.

I claim:

1. An expandable intraluminal catheter adapted to remove occlusive material from a body passage, comprising:

an elongate tubular body having a longitudinal axis and a proximal elongate tubular body end axially movable with respect to a distal elongate tubular body end;

a plurality of radially-expandable segments formed from a mesh material and disposed linearly along the longitudinal axis of the elongate tubular body between the proximal tubular body end and the distal elongate tubular body end; and a fixed element connected to the distal elongate tubular body end and extending proximally through the elongate tubular body and proximal to said proximal elongate tubular body end; and an actuator coupled to the proximal elongate tubular body end over said fixed element for actuating the plurality of radially-expandable segments by moving the proximal tubular body end relative to the fixed element and the distal tubular body end, to thereby cause each of the plurality of radially-expandable segments to radially expand into semi-rigid enlarged-diameter segments.

2. The expandable intraluminal catheter according to claim 1, wherein a width of each of the plurality of radially-expandable segments is smaller than a width of an adjacent, distally-located, radially-expandable segment, wherein each radially-expandable segment in the plurality of radially-expandable segments is progressively expanded upon actuation by the actuator, the plurality of expandable segments progressively expanding from a first distally-located expandable segment to a subsequent proximally-located expandable segment.

3. The expandable intraluminal catheter according to claim 2, wherein the expandable intraluminal catheter further comprises:

a handle coupled to the proximal elongate tubular body end and supporting said actuator, said handle having a generally open interior extending between a proximal handle end and a distal handle end; and wherein said fixed element is a wire disposed within the elongate tubular body and having a proximal end and a distal end, the proximal end of the wire being connected to the proximal handle end and the distal end of the wire being connected to the distal elongate tubular body end; whereby operation of the actuator on the handle moves the distal elongate tubular body end relative to the handle and the proximal elongate tubular body end to vary the radial size of the expandable segment.

4. The expandable intraluminal catheter according to claim 3, wherein;

the elongate tubular body has a lumen along the longitudinal axis of the elongate tubular body;

the wire is disposed in the lumen; and the actuator moves the proximal elongated tubular body end proximally to radially expand the plurality of radially expandable segments by moving the proximal elongate tubular body end over said wire toward the distal elongate tubular body end, and moves the proximal elongated tubular body end distally to radially contract the plurality of radially expandable segments by moving the proximal elongate tubular end over said wire away from the distal elongate tubular body end.

5. The expandable intraluminal catheter according to claim 4, wherein apertures are formed on each of the plurality of radially expandable segments in response to expansion of the segments by the actuator, to thereby allow for application of one of a pressure and a suction to the apertures.

6. The expandable intraluminal catheter according to claim 5, wherein the proximal handle end comprises a port, which is connected to the lumen, and wherein one of a pressure and a suction is applied to the apertures through the port.

7. The expandable intraluminal catheter according to claim 6, wherein the port in the proximal handle end comprises a luer type locking hub, which allows fluid to be inserted into the lumen to be excreted through the apertures, and which allows fluid to be drawn through the apertures and out of the lumen.

8. The expandable intraluminal catheter according to claim 1, wherein the plurality of radially-expandable segments are separated by a corresponding plurality of non-expandable segments, which are disposed between the plurality of radially-expandable segments on the elongate tubular body.

9. The expandable intraluminal catheter according to claim 8, wherein, when the radially-expandable segments are not radially expanded, the plurality of radially-expandable segments and the corresponding plurality of non-expandable segments form a relatively smooth surface on an exterior surface of the elongate tubular body to thereby allow the elongate tubular body to move within the body passage with relative ease.

10. The expandable intraluminal catheter according to claim 9, wherein a width, measured in a direction parallel to the longitudinal axis of the elongate tubular body, of each of the plurality of radially-expandable segments is greater than a width of a corresponding adjacent one of the plurality of non-expandable segments.

11. The expandable intraluminal catheter according to claim 10, wherein the actuator causes the plurality of radially-expandable segments to radially expand into semi-rigid enlarged-diameter segments, by moving the proximal elongate tubular body end and the distal elongate tubular body end toward one another, over said fixed element wherein the larger widths, measured in a direction parallel to the longitudinal axis of the elongate tubular body, of the radially-expandable segments are attenuated as the radially expandable segments radially expand, and wherein the smaller widths of the non-expandable segments do not attenuate as the non-expandable segments do not radially expand.

12. The expandable intraluminal catheter according to claim 11, wherein the plurality of radially-expandable segments and the corresponding plurality of non-expandable segments are integrally formed with the exterior surface of the elongate tubular body, each radially-expandable segment being joined to an adjacent non-expandable segment at a bendable joint.

13. The expandable intraluminal catheter according to claim 11, wherein each of the plurality of radially-expandable mesh segments comprises an expandable, plastic, tubular braid and each of the corresponding plurality of non-expandable segments comprises a semi-rigid plastic tubing.

14. An expandable intraluminal catheter adapted to remove occlusive material from a body passage, comprising:

a hollow handle having a proximal handle end and a distal handle end;

an elongate tubular body having a proximal elongate tubular body end disposed within the hollow handle and movable relative to a distal elongate tubular body end, and a lumen extending between the proximal elongate tubular body end and the distal elongate tubular end;

a plurality of radially-expandable segments disposed axially along the elongate tubular body between the proximal elongate tubular body end and the distal elongate tubular body end;

an expandable distal member, located on the elongate tubular body between the distal elongate tubular body end and the plurality of radially-expandable segments;

a non-expandable member disposed within the lumen of the elongate tubular body, the non-expandable member having a proximal non-expandable member end connected to said handle and a distal non-expandable member end connected to the distal elongate tubular body end; and an actuator coupled to said proximal tubular body end through said hollow handle for actuating the plurality of radially expandable segments and the expandable distal member to radially expand in response to movement of the proximal elongate tubular body end over said non-expandable member toward the distal elongate tubular body end and to radially contract in response to movement of the proximal elongate tubular end over said non-expandable member away from the distal elongate tubular body end.

15. The expandable intraluminal catheter according to claim 14, wherein the actuator causes the plurality of radially-expandable segments to progressively radially expand, the plurality of radially-expandable segments progressively radially expanding from a first distally-located expandable segment to a proximally-located expandable segment.

16. The expandable intraluminal catheter according to claim 15, wherein the actuator moves the proximal elongate tubular body end relative to the distal elongate tubular body end to cause the plurality of radially-expandable segments to progressively radially expand, the plurality of radially-expandable segments progressively radially expanding from both a first distally-located expandable segment and a second proximally-located expandable segment toward a central region between said first and second radially expandable segments to thereby move the occlusive material toward the central region.

17. The expandable intraluminal catheter according to claim 14, wherein the expandable distal member comprises an inflatable balloon, which, when inflated, is deformable from an elongated shape into a generally spherical shape.

18. An expandable intraluminal catheter adapted to remove occlusive material from a body passage, comprising:

a hollow handle having a proximal handle end and a distal handle end;

an elongate tubular body having a proximal elongate tubular body end disposed within the hollow handle and movable relative to a distal elongate tubular body end, and a lumen extending between the proximal elongate tubular body end and the distal elongate tubular end;

a plurality of radially-expandable segments disposed axially along the elongate tubular body between the proximal elongate tubular body end and the distal elongate tubular body end;

an expandable distal member located on the elongate tubular body between the distal elongate tubular body end and the plurality of radially-expandable segments;

a non-expandable member disposed within the lumen of the elongate tubular body, the non-expandable member having a proximal non-expandable member end connected to said handle and a distal non-expandable member end connected to the distal elongate tubular body end;

an actuator coupled to said proximal tubular body end through said hollow handle for actuating the plurality of radially expandable segments and the expandable distal member to radially expand in response to movement of the proximal elongate tubular body end over said non-expandable member toward the distal elongate tubular body ends and to radially contract in response to movement of the proximal elongate tubular end over said non-expandable member away from the distal elongate tubular body end; and the expandable distal member comprises a elastomeric foam, which, when expanded by the actuator, is deformable from an elongated shape into a generally spherical shape.

* * * * *